US00PP22008P2

(12) United States Plant Patent
Herrera Valenzuela et al.

(10) Patent No.: US PP22,008 P2
(45) Date of Patent: Jul. 5, 2011

(54) ***ALSTROEMERIA* PLANT NAMED 'JAVE'**

(50) Latin Name: *Alstroemeria hybrida*
Varietal Denomination: Jave

(75) Inventors: Camilo Herrera Valenzuela, Bogotá (CO); Henry Belalcázar Valencia, Bogotá (CO)

(73) Assignee: C.I. Valmar S.A., Bogotá (CO)

( * ) Notice: Subject to any disclaimer, the term of this patent is extended or adjusted under 35 U.S.C. 154(b) by 0 days.

(21) Appl. No.: 12/660,119

(22) Filed: Feb. 19, 2010

(51) Int. Cl.
*A01H 5/00* (2006.01)

(52) U.S. Cl. ..... Plt./309

(58) Field of Classification Search ..... Plt./309
See application file for complete search history.

*Primary Examiner* — June Hwu
(74) *Attorney, Agent, or Firm* — C. A. Whealy

(57) ABSTRACT

A new and distinct cultivar of *Alstroemeria* plant named 'Jave', characterized by its erect and strong flowering stems; vigorous growth habit; large dark yellow-colored flowers with dark greyed purple-colored flecks and streaks, flowers arranged in symmetrical umbels; and excellent postproduction longevity.

1 Drawing Sheet

Botanical designation: *Alstroemeria hybrida.*
Cultivar denomination: 'JAVE'.

BACKGROUND OF THE INVENTION

The present invention relates to a new and distinct cultivar of *Alstroemeria* plant, botanically known as *Alstroemeria hybrida*, commercially used as a cut flower *Alstroemeria*, and hereinafter referred to by the name 'Jave'.

The new *Alstroemeria* plant is a product of a planned breeding program conducted by the Inventors in Madrid, Cundinamarca, Colombia. The objective of the breeding program was to create new *Alstroemeria* cultivars with desirable plant qualities, attractive flower color and excellent postproduction longevity.

The new *Alstroemeria* plant originated from a cross-pollination conducted in March, 2005 by the Inventors in Madrid, Cundinamarca, Colombia of a proprietary selection of *Alstroemeria hybrida* identified as code number PS 447, not patented, as the female, or seed, parent with a proprietary selection of *Alstroemeria hybrida* identified as code number HH 124, as the male, or seed, parent. The new *Alstroemeria* plant was discovered and selected by the Inventors as a single flowering plant from within the progeny of the stated cross-pollination grown in a controlled greenhouse environment in Madrid, Cundinamarca, Colombia in January, 2007.

Asexual reproduction of the new *Alstroemeria* plant by rhizome divisions in a controlled greenhouse environment in Madrid, Cundinamarca, Colombia since April, 2007, has shown that the unique features of this new *Alstroemeria* plant are stable and reproduced true to type in successive generations.

SUMMARY OF THE INVENTION

Plants of the new *Alstroemeria* have not been observed under all possible environmental and cultural conditions. The phenotype may vary somewhat with variations in environment and cultural practices such as temperature and light intensity without, however, any variance in genotype.

The following traits have been repeatedly observed and are determined to be the unique characteristics of 'Jave'. These characteristics in combination distinguish 'Jave' as a new and distinct cultivar of *Alstroemeria* plant:

1. Erect and strong flowering stems.
2. Vigorous growth habit.
3. Large dark yellow-colored flowers with dark greyed purple-colored flecks and streaks, flowers arranged in symmetrical umbels.
4. Excellent postproduction longevity.

Plants of the new *Alstroemeria* can be compared to plants of the parent selections. Plants of the new *Alstroemeria* differ from plants of the parent selections primarily in flower color as plants of the parent selections have yellow orange-colored flowers.

Plants of the new *Alstroemeria* can be compared to plants of *Alstroemeria hybrida* 'Zalsadim', disclosed in U.S. Plant Pat. No. 15,985. In side-by-side comparisons plants of the new *Alstroemeria* differed primarily from plants of 'Zalsadim' in the following characteristics:

1. Plants of the new *Alstroemeria* had smaller inflorescences than plants of 'Zalsadim'.
2. Plants of the new *Alstroemeria* had larger flowers with larger perianth segments than plants of 'Zalsadim'.
3. Plants of the new *Alstroemeria* and 'Zalsadim' differed slightly in flower color.
4. Plants of the new *Alstroemeria* had shorter pedicels than plants of 'Zalsadim'.
5. Plants of the new *Alstroemeria* and 'Zalsadim' differed in anther color.
6. Plants of the new *Alstroemeria* and 'Zalsadim' differed in style, stigma and ovary color.

BRIEF DESCRIPTION OF THE PHOTOGRAPHS

The accompanying colored photographs illustrate the overall appearance of the new *Alstroemeria* plant, showing the colors as true as it is reasonably possible to obtain in colored reproductions of this type. Colors in the photographs may differ slightly from the color values cited in the detailed botanical description which accurately describe the colors of the new *Alstroemeria* plant.

The photograph at the bottom of the sheet comprises a side perspective view of a typical flowering stem of 'Jave'.

The photograph at the top of the sheet is a close-up view of a typical inflorescence of 'Jave'.

DETAILED BOTANICAL DESCRIPTION

The aforementioned photographs and following observations and measurements describe plants of the new *Alstroemeria* grown in Madrid, Cundinamarca, Colombia in a polyethylene-covered greenhouse in ground beds. During the production of the plants, maximum day temperatures averaged 31.5° C., maximum night temperatures averaged 6° C. and light levels averaged 21.4 KWH/m$^2$. Plants used for the photographs and description were one year old. Color references are made to The Royal Horticultural Society Colour Chart, 2007 Edition, except where general terms of ordinary dictionary significance are used.

Botanical classification: *Alstroemeria hybrida* 'Jave'.

Parentage:

*Female, or seed, parent.*—Proprietary selection of *Alstroemeria hybrida* identified as code number PS 447, not patented.

*Male, or pollen, parent.*—Proprietary selection of *Alstroemeria hybrida* identified as code number HH 124.

Propagation:

*Type.*—By rhizome divisions.

*Time to initiate roots.*—About two weeks at temperatures ranging from about 6° C. to 32° C.

*Time to produce a rooted young plant.*—About eight weeks at temperatures ranging from about 6° C. to 32° C.

*Root description.*—Fleshy, medium in thickness; close to 155A in color.

*Rooting habit.*—Freely branching; dense.

*Rhizomes.*—Shape: Rounded. Length: About 15 cm. Diameter: About 1.49 cm. Texture: Fleshy. Color: Close to NN155A.

Plant description:

*Plant and growth habit.*—Upright; freely branching, bushy appearance; vigorous growth habit.

*Time from planting to harvest of cut flowers.*—About 18 weeks.

Flowering stem description:

*Aspect.*—Erect.

*Length.*—About 130 cm to 155 cm.

*Diameter.*—About 6 mm.

*Internode length.*—About 3 cm to 5 cm.

*Strength.*—Strong.

*Texture.*—Smooth, glabrous.

*Color.*—Close to 146C.

Foliage description:

*Arrangement.*—Alternate, simple.

*Length.*—About 11.8 cm.

*Width.*—About 3.1 cm.

*Shape.*—Oblanceolate.

*Apex.*—Acute.

*Base.*—Attenuate.

*Margin.*—Entire.

*Texture, upper and lower surfaces.*—Smooth, glabrous; longitudinally ridged.

*Venation pattern.*—Parallel.

*Color.*—Developing leaves, upper and lower surfaces: Close to 146C. Fully expanded leaves, upper surface: Close to 146A; venation, close to 146C. Fully expanded leaves, lower surface: Close to 147B; venation, close to 146B.

*Petioles.*—Length: About 3.6 cm. Diameter: About 5 mm Texture, upper and lower surfaces: Smooth, glabrous. Color, upper and lower surfaces: Close to 146B to 146C.

Flower description:

*Flower type and arrangement.*—Single cup-shaped flowers arranged in compound umbels; flowers face upright to outwardly; perianth segments separate.

*Flowering habit.*—Freely flowering with about 15 open flowers and flower buds per inflorescence.

*Natural flowering season.*—Flowering continuous year round in a greenhouse in Colombia; plants begin flowering about 18 weeks after planting.

*Fragrance.*—None detected.

*Flower longevity as a cut flower.*—About two weeks; flowers not persistent.

*Flower buds (showing color).*—Length: About 3.5 cm. Diameter: About 1.3 cm. Shape: Obovate. Color: Close to 145A to 145B.

*Umbel height.*—About 18.5 cm.

*Umbel diameter.*—About 17 cm by 18 cm.

*Flower diameter.*—About 6.5 cm.

*Flower length (height).*—About 7.5 cm.

*Flower depth.*—About 6.5 cm.

*Perianth.*—Arrangement: Six arranged in two whorls, each whorl with two lateral and one median segments. Inner perianth, lateral segments: Length: About 6.8 cm. Width: About 1.5 cm. Shape: Oblanceolate. Apex: Mucronate. Base: Attenuate. Margin: Entire. Texture, upper and lower surfaces: Smooth, glabrous; satiny. Color, when opening, upper surface: Towards the apex, close to 14A; towards the base, close to 12A to 12B. Color, when opening, lower surface: Close to 14B to 14C. Color, fully opened, upper surface: Towards the apex, close to 14A to 14B; towards the base, close to 14C to 14D; flecks and streaks, close to 185A. Color, fully opened, lower surface: Towards the apex, close to 13A to 13B; toward the base, close to 13C to 13D. Inner perianth, median segment: Length: About 6.1 cm. Width: About 1.5 cm. Shape: Oblanceolate. Apex: Mucronate. Base: Attenuate. Margin: Entire. Texture, upper and lower surfaces: Smooth, glabrous; satiny. Color, when opening, upper surface: Towards the apex, close to 13A to 13B, towards the base, close to 13C to 13D. Color, when opening, lower surface: Close to 13B to 13D. Color, fully opened, upper surface: Towards the apex, close to 14A to 14B; towards the base, close to 14C to 14D; few flecks and streaks, close to 185A. Color, fully opened, lower surface: Towards the apex, close to 14A to 14B; towards the base, close to 13C to 13D. Outer perianth, lateral segments: Length: About 6 cm. Width: About 2.8 cm. Shape: Obovate to elongated cordate. Apex: Emarginate to cordate. Base: Attenuate. Margin: Entire. Texture, upper and lower surfaces: Smooth, glabrous; satiny. Color, when opening, upper surface: Towards the apex, close to 13A to 13B; towards the base, close to 13C to 13D. Color, when opening, lower surface: Towards the apex and margins, close to 13B; towards the base, close to 13D; venation, close to 144B. Color, fully opened, upper surface: Towards the apex, close to 13A to 13B;

towards the base, close to 13C to 13D; with development color becomes closer to 23B. Color, fully opened, lower surface: Close to 13C; towards the base, close to 13D; venation, close to 144B. Outer perianth, median segment: Length: About 6 cm. Width: About 2.7 cm. Shape: Obovate to elongated cordate. Apex: Emarginate to cordate. Base: Attenuate. Margin: Entire. Texture, upper and lower surfaces: Smooth, glabrous; satiny. Color, when opening, upper surface: Towards the apex, close to 13A to 13B; towards the base, close to 13C to 13D. Color, when opening, lower surface: Towards the apex and margins, close to 13B; towards the base, close to 13D; venation, close to 144B. Color, fully opened, upper surface: Towards the apex, close to 13A to 13B; towards the base, close to 13C to 13D; with development color becomes closer to 23B. Color, fully opened, lower surface: Close to 13C; towards the base, close to 13D; venation, close to 144B.

*Pedicels.*—Length: About 2.7 cm. Diameter: About 2 mm. Strength: Strong. Angle: About 25° to 35° from the peduncle axis. Texture: Smooth, glabrous. Color: Close to 146B.

*Reproductive organs.*—Stamens: Quantity per flower: Six. Anther shape: Elongated. Anther length: About 8 mm. Anther diameter: About 2 mm. Anther color: Close to 152D. Pollen amount: Moderate. Pollen color: Close to 15A. Pistils: Quantity per flower: One. Pistil length: About 5.4 cm. Style length: About 4 cm. Style color: Close to 4B to 4D. Stigma shape: Three-parted. Stigma color: Close to 4A. Ovary color: Close to 144A.

*Fruit/seed.*—Fruit and seed development has not been observed.

Disease/pest resistance: Plants of the new *Alstroemeria* have not been observed to be resistant to pathogens and pests common to *Alstroemeria.*

It is claimed:

1. A new and distinct *Alstroemeria* plant named 'Jave' as illustrated and described.

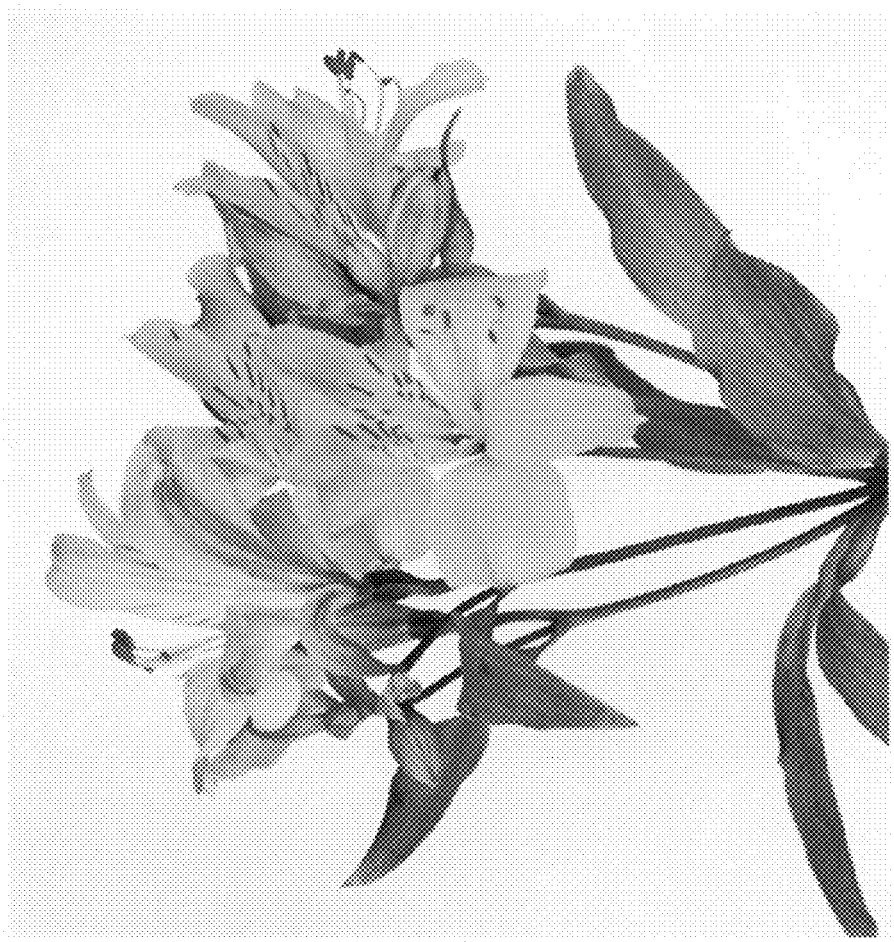
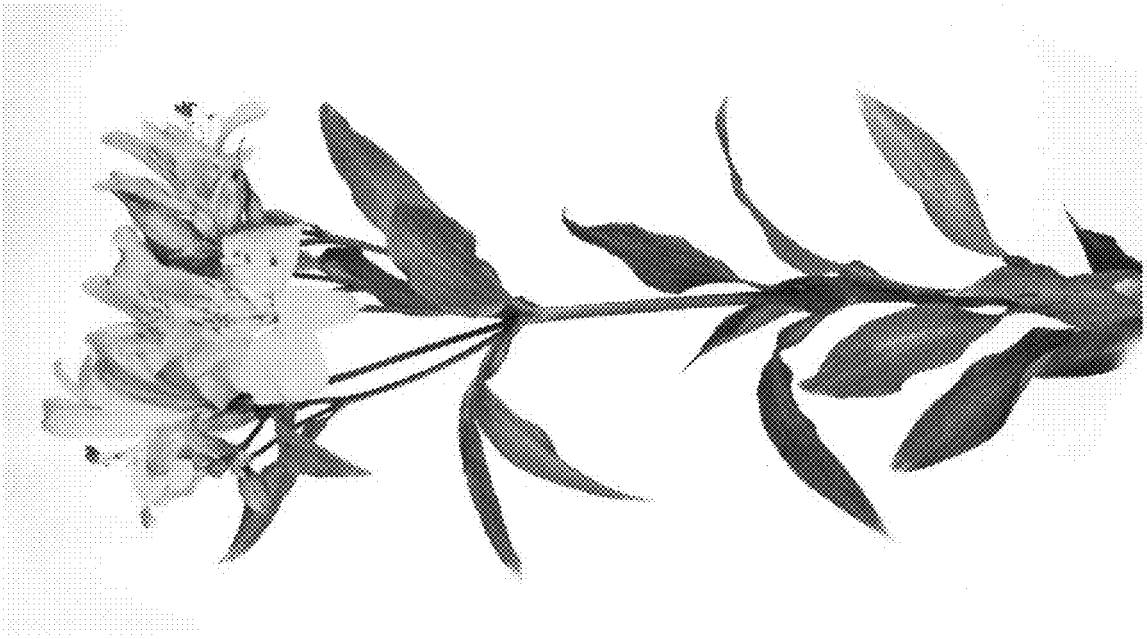

* * * * *